US00PP13924P29

(12) United States Plant Patent
Ibes

(10) Patent No.: US PP13,924 P2
(45) Date of Patent: Jul. 1, 2003

(54) SAINTPAULIA PLANT NAMED 'INA'

(75) Inventor: Wim J. M. Ibes, Herveld (NL)

(73) Assignee: Handelskwekerij "De Eeuwige Lente", Herveld (NL)

( * ) Notice: Subject to any disclaimer, the term of this patent is extended or adjusted under 35 U.S.C. 154(b) by 0 days.

(21) Appl. No.: 10/036,430

(22) Filed: Jan. 7, 2002

(51) Int. Cl.[7] ..... A01H 5/00

(52) U.S. Cl. ..... Plt./268

(58) Field of Search ..... Plt./268, 269

*Primary Examiner*—Kent Bell
(74) *Attorney, Agent, or Firm*—Foley & Lardner

(57) ABSTRACT

A new and distinct Saintpaulia plant named 'Ina', illustrated and described and particularly characterized by its better growing characteristics; full rosette form of the flowers; intense purple color of the flowers; and contrasting white petal margins.

2 Drawing Sheets

Latin name of the genus and species of the plant claimed: *Saintpaulia ionantha.*

Variety denomination: 'Ina'.

BACKGROUND OF THE INVENTION

The present invention relates to a new and distinct cultivar of Saintpaulia or African Violet, botanically known as *Saintpaulia ionantha,* and hereinafter referred to by the cultivar name 'Ina'.

The new cultivar originated from a cross made by the inventor, Wim J. M. Ibes, in a controlled breeding program in the village of Herveld, the Netherlands. The female parent is an unnamed proprietary seedling with breeder's reference '96-10-2' (unpatented). The male parent is an unnamed proprietary seedling with breeder's reference 'A 155' (unpatented). In comparison to 'Ina', the female parent, '96-10-2', has star-like shaped flowers with white margins, and the male parent, 'A 155', is a single flowering Saintpaulia with a dark-blue flower color and long-lasting qualities. 'Ina' was discovered and selected by the inventor, within the progeny of the stated cross in a controlled environment in the village of Herveld, the Netherlands.

'Ina' is a product of a planned breeding program conducted by the Inventor and selected in a cultivated environment in the village of Herveld. The objective of the breeding program was to develop Saintpaulia varieties with better growing characteristics, new flower colors and a better lasting quality of the plants. Asexual reproduction of the new cultivar by leaf cuttings was first performed in June 1999 in the village of Herveld, the Netherlands and has demonstrated that the combination of characteristics as herein disclosed for the new cultivar are firmly fixed and reproduce true to type in successive generations of asexual reproduction.

BRIEF SUMMARY OF THE INVENTION

The following traits have been repeatedly observed and are determined to be basic characteristics of 'Ina' which in combination distinguish this Saintpaulia as a new and distinct cultivar:

1. better growing characteristics;
2. full rosette form of the flowers;

3. intense purple color of the flowers; and
4. contrasting white leaf margins.

'Ina' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in the village of Herveld in the greenhouse at average growing temperatures of 20 degrees centigrade and the use of supplementary light under conditions which closely approximate those generally used in commercial practice.

Of the many commercial cultivars known to the present inventor, no cultivars can be compared to cultivar 'Ina'.

BRIEF DESCRIPTION OF THE DRAWING

The accompanying photographic illustrations show a typical plant of Saintpaulia 'Ina' with colors as true as possible with illustrations of this kind.

The first drawing shows a mature grown plant showing its characteristics in full rosette form.

The second drawing shows detail of the plant presenting the half-double flowers with remarkable white petal margins.

DETAILED BOTANICAL DESCRIPTION

The following observations, measurements and values describe the new cultivar at 10 weeks, as a full grown plant, in a 10–11 centimeter pot, as grown in the village of Herveld, the Netherlands, in September 2001, under conditions which closely approximate those generally used in commercial practice. The plants are grown under controlled climate conditions in a greenhouse including the use of supplementary lights at an average temperature of 20 degrees centigrade. Color references are made to The Royal Horticultural Society Colour Chart (R.H.S.), except where general colors of ordinary significance are used. Color values were taken under daylight conditions at approximately 12:00 noon in the greenhouse in the village of Herveld, the Netherlands.

Parentage:

*Male parent.*—Unnamed proprietary seedling breeder's reference 'A 155'.

*Female parent.*—Unnamed proprietary seedling breeder's reference '96-10-2'.

Propagation:

*Method of asexual reproduction.*—Leaf cutting.

Plant:

General appearance and form:

*Height.*—10 cm as measured from the soil level the top of the flowers of a plant grown in a 11 cm pot.

*Width.*—28 cm.

*Growth habit and rate.*—Plants are full grown at 10 weeks after planting of a rooted cutting in a container.

*Winter hardiness.*—Cold damage to plant in temperatures below 12° C.

*Plant vigor.*—Average when compared to commercially grown Saintpaulia varieties.

*Rooting habit.*—Comparable to commercially grown Saintpaulia varieties.

*Blooming habit.*—Comparable to commercially grown Saintpaulia varieties.

*Blooming period.*—All year round.

Foliage:

*Arrangement.*—Rosette.

*Type.*—About 30 leaves rounded.

*Color.*—Young foliage: Upper side: RHS 137-A. Under side: RHS 77-A. Venation upper side: RHS 137-A. Venation under side: RHS 71-A. Mature foliage: Upper side: RHS 137-A. Under side: RHS 138-D. Venation upper side: RHS 137-D. Venation under side: RHS 138-D. Length: 8 cm. Width: 7 cm. Shape: Rounded. Leaf apex: Rounded. Leaf base: Double lobes. Texture: Papilose and pilose. Quantity of leaves: 30. Midrib color: RHS 199-D (under side).

*Petioles.*—Quantity: 30. Shape: Elongated. Color: RHS 64-D. Size: Length 7 cm.; diameter 0.7 cm.

Flowers:

*Form/arrangement.*—Rosette.

*Flower appearance.*—Upright.

*Longevity.*—28 days.

*Quantity.*—8 peduncles including an average of 12 flowers each.

*Flower type.*—Half-double.

*Petal count.*—Average of 5 when flower matures.

*Petals.*—Rounded to oval shape; length 1 cm; width 1 cm when mature; papillose; upper side color RHS 89-B; color of margin RHS 155-C; lower side color RHS 89D.

*Sepals.*—From the center of the flower, a wreath of 5 sepals are formed, the lower 3 sepals are 1.5 cm in length and the upper 2 sepals are 1 cm in length; another 4–5 sepals are formed within the center of flower (giving it the half-double flower type characteristic), which are smaller and curled with the length and width between 0.5 and 1 cm.

*Peduncle.*—Length 7.5 cm.; diameter 0.4 cm.; elongated; pilose; color RHS 62-D.

*Flower bud.*—Shape is globule; length 0.7 cm.; width 0.7 cm.; color RHS 83-B.

Roots:

*Time to initiate roots.*—14 days at 20 degrees centigrade.

*Time to develop roots.*—8 weeks at 20 degrees centigrade.

*Rooting habit.*—Fine and freely branching.

Reproductive organs:

*Stamens.*—Length 0.3 cm.; diameter 0.1 cm.; color RHS 4-B; filaments: color RHS 4-A; Anther length 0.2 cm.; diameter 0.3 cm.; color RHS 5-A.

*Pollen.*—RHS 4-D in color; scarce production.

*Pistils.*—Quantity 1; color RHS 86-C; Stigma color RHS 85-C; ovary color RHS 85-D.

*Seed development.*—None.

Disease resistance/susceptibility: No observations to date.

I claim:

1. A new and distinct Saintpaulia plant named 'Ina', substantially as illustrated and described herein.

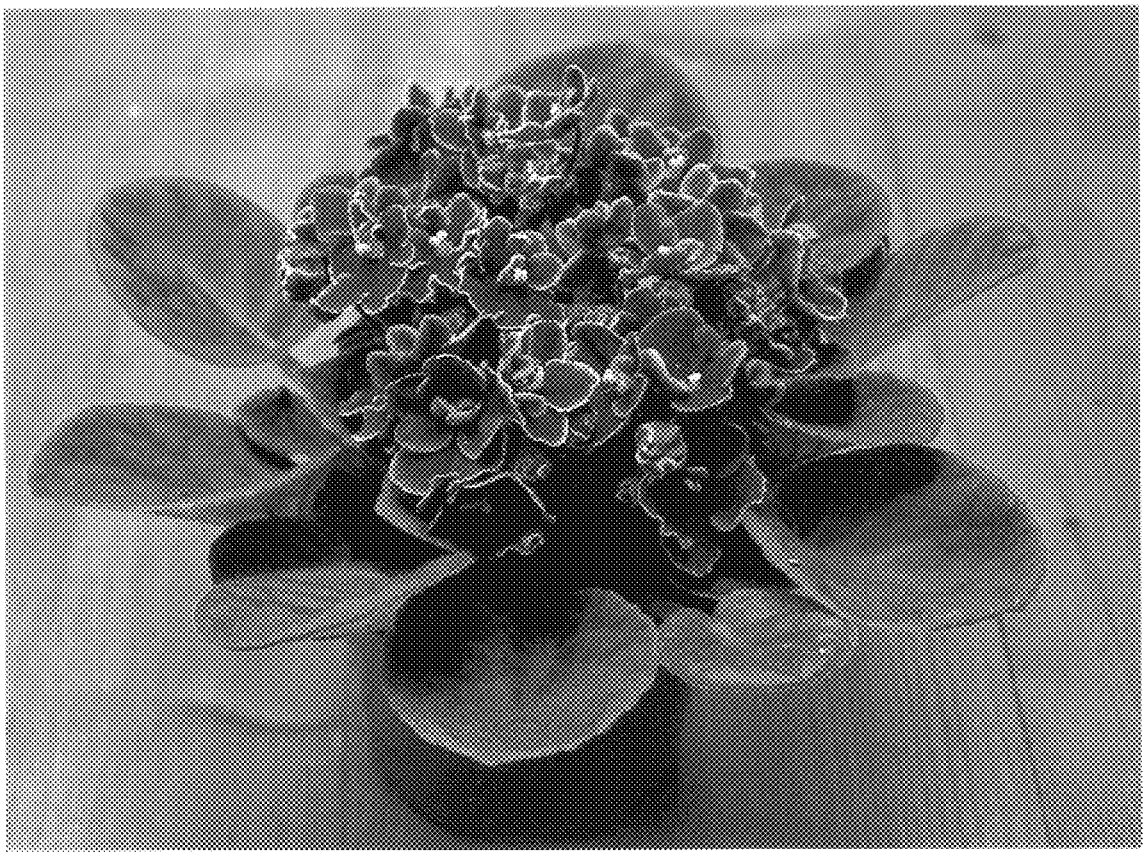

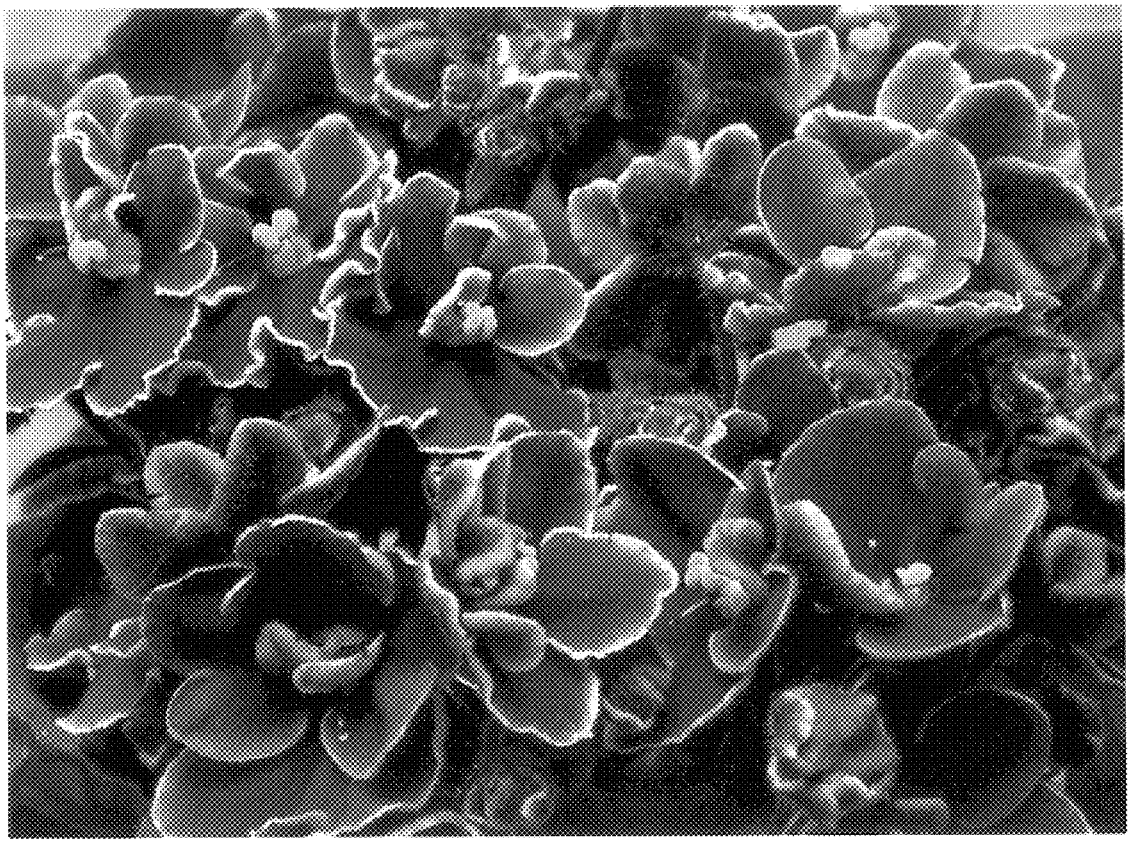

* * * * *